(12) United States Patent
Kopelman et al.

(10) Patent No.: US 6,664,986 B1
(45) Date of Patent: Dec. 16, 2003

(54) COMPUTER USER INTERFACE FOR ORTHODONTIC USE

(75) Inventors: Avi Kopelman, Ramat-Chen (IL); Baruch Nissenbaum, Ramat Gan (IL)

(73) Assignee: Cadent Ltd., Or Yehuda (IL)

( * ) Notice: Subject to any disclaimer, the term of this patent is extended or adjusted under 35 U.S.C. 154(b) by 0 days.

(21) Appl. No.: 09/424,167

(22) PCT Filed: May 19, 1998

(86) PCT No.: PCT/IL98/00222
§ 371 (c)(1),
(2), (4) Date: May 30, 2000

(87) PCT Pub. No.: WO98/53428
PCT Pub. Date: Nov. 26, 1998

(30) Foreign Application Priority Data

May 20, 1997 (IL) ................................................. 120867

(51) Int. Cl.[7] .......................... G06T 17/40; G06F 3/033
(52) U.S. Cl. ...................... 345/849; 345/848; 345/815; 345/653; 345/658; 378/38; 433/68
(58) Field of Search ................................ 345/419, 653, 345/581, 619, 849, 848, 815; 433/213, 68; 378/38; 348/66

(56) References Cited

U.S. PATENT DOCUMENTS

| | | | | |
|---|---|---|---|---|
| 5,605,459 A | * | 2/1997 | Kuroda et al. | 433/214 |
| 5,776,050 A | * | 7/1998 | Chen et al. | 600/117 |
| 6,072,478 A | * | 6/2000 | Kurihara et al. | 715/500.1 |
| 6,084,979 A | * | 7/2000 | Kanade et al. | 382/154 |

FOREIGN PATENT DOCUMENTS

| | | |
|---|---|---|
| EP | 0 658 839 A2 | 11/1994 |
| WO | WO 94/10935 | 5/1994 |

OTHER PUBLICATIONS

International Search Report; International Application No. PCT/IL 98/00222; Mar. 9, 1998.
"Method and System for Acquiring Three–Dimensional Teeth Image", Patent No. WO 97/03622; Kopelman et al., Document bibliography, abstract and claims.

* cited by examiner

Primary Examiner—John Cabeca
Assistant Examiner—Namitha Pillai
(74) Attorney, Agent, or Firm—Nath & Associates PLLC; Gary M. Nath; Marvin C. Berkowitz

(57) ABSTRACT

In a computer system that includes a Central Processing Unit and an associated input device, storage device and display device, a method for displaying on the display device a virtual three-dimensional (3D) dental model at desired pre-set views, for orthodontic use. The virtual 3D dental model is stored on the storage device and is indicative of a 3D structure of an individual's dental arches. The method includes the steps of providing a graphic user interface (GUI) that includes a graphic representation of the dental model and a plurality of graphic symbols each representative of a desired pre-set view of the dental model from a desired direction. Selecting through the input device graphic symbol from among the plurality of graphic symbols. Moving the dental model to a pre-set view which corresponds to the graphic symbol, whilst retaining the model in zoom.

33 Claims, 4 Drawing Sheets

COMPUTER USER INTERFACE FOR ORTHODONTIC USE

FIELD OF THE INVENTION

The present invention concerns viewing a three-dimensional (3D) object or portion thereof from a desired direction.

BACKGROUND OF THE INVENTION

Generally speaking, the manipulating of a computerized 3D image of a real-world object, is a very complicated task. The ever increasing need for such 3D manipulations, in various scientific and entertainment oriented applications, has encouraged the development of appropriate tools, and indeed many software tools, adapted for 3D manipulation, can be found in the marketplace, such as Auto-CAD, ver 13.0, commercially available from Autodesk. Inc.

Whilst Auto-CAD, (or similar tools), indeed provides a wide-range of manipulating features, it normally necessitates a long-term training period before it can be used effectively.

For appropriate Orthodontic diagnostics, the orthodontist is required to analyze a three dimensional structure of the individual dental arches (including the individual teeth) inter alia by observing the specified 3D structure from various preset views, e.g. from various directions around he virtual model, tilting the 3D structure, opening and closing the dental arches, and others.

A plaster model representative of the individual's 3D morphology of his/her dental arches is a common tool that is utilized to this end. The plaster model has, however, some drawbacks such as it being fragile i.e. it may be damaged due to inadvertent faulty care. Moreover, in order to evaluate the progress of orthodontic treatment of an individual, it is desired to compare and derive the discrepancies between two consecutive plaster models of the 3D morphology of the individuals dental arches. This task is very difficult when evaluating in a traditional manner the so obtained consecutive plaster models.

The latter drawbacks and others have encouraged the development of technology which provides for a virtual 3D model of the individual dental arch morphology (hereinafter virtual 3D dental model) that is represented in the computer and does not suffer from the limitation of a tangible physical model. The virtual dental model, as being a digital entity, can be stored on a storage medium, retrieved whenever required, duplicated and transmitted to a different remote site.

A technique for generating and storing a virtual 3D dental model in the computer is described, e.g. in WO 97/03622 published on Feb. 6, 1997.

Viewing the virtual 3D dental model from desired directions and applying other manipulation to said image are possible, by utilizing traditional image manipulation tools, such as the specified AutoCAD. The latter, however, are effectively impractical for use by average orthodonts and other lab personal, who normally lack the adequate computer oriented background required to activate the complicated sequence of operations, in the specified software tool, which will eventually result in bringing the virtual image to the desired orientation.

For a better understanding of the foregoing, attention is now directed to FIGS. 1A and 1B illustrating two subsequent rotation of a virtual 3D dental image with a 45 degree shift one with respect to the other.

In order to accomplish the movement of the virtual 3D dental model from the view of FIG. 1A to the view of FIG. 1B, whilst maintaining the respective images in optimized zoom and elevation, a specific set of instructions, should be invoked. There follows a brief description of the relevant commands which will serve, inter alia for accomplishing the specified model manipulation.

Thus, in order to obtain a view of the model from a desired view point one should specify the desired view point in terms of two angles, one with respect to the X axis (in the XY plane), and the "elevation from the XY plane.

Next, one should "zoom" the view to the extent of the display.

Of course a pre-calculation of the desired angle should be performed manually.

Thus, the relevant commands are:

VPOINT>CR

ROTATE>CR

ANGLE IN XY PLANE>45 CR (where 45 stands for the desired angle)

ANGLE FROM XY PLANE>30 CR (where 30 stands for the desired angle)

ZOOM>CR

EXTENDS>EXTENDS CR

It is accordingly understood that realizing e.g. a continuous motion around the model e.g. from the view of FIG. 1A to the view of FIG. 1B, is a very complicated procedure in accordance with the specified AutoCAD tool.

Those versed in the art will readily appreciate that an average orthodont who is not a skilled operator of the AutoCAD software tool (or any other sophisticated 3D manipulation utility), will not be able to utilize such a complicated tool.

In the context of the invention, optimal zoom is defined as essentially maintaining the entire model view on the screen and preferably also depicting the model at essentially the same location on the screen, after the model has been subject to manipulation.

It is accordingly the object of the present invention to provide a user friendly Graphical User Interface (GUI), which will enable even the most inproficient user to readily be able to manipulate a virtual 3D dental model between preset views that are commonly required for orthodontic treatment.

SUMMARY OF THE INVENTION

It is an important finding of the invention that the orthodont, during normal and daily use, is interested in well defined pre-set views of a virtual 3D dental model for accomplishing orthodontic treatment and accordingly a very simple and intuitive graphic user interface (GUI), is introduced in order to enable even the most in-proficient user to easily manipulate the virtual 3D dental model, and in this manner to achieve two fold advantage. On the one hand, benefiting from the advantages of manipulating virtual dental image as compared to tangible fragile model, and on the other hand, benefiting from easy and straight forward manipulation procedures essentially as if the virtual model were a physical model.

Accordingly, the present invention provides for: in a computer system comprising a Central Processing Unit and an associated input device, storage means and display device, a method for displaying on said display device a virtual three dimensional (3D) dental model at desired pre-set views, for orthodontic use; the virtual 3D dental model is stored on said storage means and is indicative of at least a 3D structure of an individual's dental arches; the method comprising the steps of:

(a) providing a graphic user interface (GUI) that includes a graphic representation of the dental model and a plurality of graphic symbols each representative of at least one desired pre-set view of the dental model or a portion thereof from respective desired directions;

(b) selecting by means of said input device a graphic symbol from among said plurality of graphic symbols;

(c) responsive to the selection of said graphic symbol, moving the dental model or portion thereof to at least one pre-set view which corresponds to said graphic symbol, whilst retaining the model essentially in zoom.

The present invention further provides for a computer system comprising a Central Processing Unit and an associated input device, storage means and display device, the computer system is adapted to display on said display device a virtual three dimensional (3D) dental model at desired pre-set views, for orthodontic use; the virtual 3D dental model is stored on said storage means and is indicative of at least a 3D structure of an individual's dental arches; the computer system comprising:

(a) a graphic user interface (GUI) that includes a graphic representation of the dental model and a plurality of graphic symbols each representative of at least one desired pre-set view of the dental model or a portion thereof from respective desired directions;

(b) means responsive to activation of said input device for selecting a graphic symbol from among said plurality of graphic symbols;

(c) means responsive to the selection of said graphic symbol, for moving the dental model or portion thereof to at least one pre-set view which corresponds to said graphic symbol, whilst retaining the model essentially in zoom.

Still further the invention provides for a memory for storing data indicative of a graphic user interface (GUI), for access by a user in order to activate application program for orthodontic use;

said GUI includes a graphic representation of a dental model and a plurality of graphic symbols each representative of at least one desired pre-set view of the dental model or a portion thereof from respective desired directions;

said dental model is indicative of at least a 3D structure of an individual's dental arches.

BRIEF DESCRIPTION OF THE DRAWINGS

For a better understanding, the invention will now be described, by way of example only, with reference to the accompanying drawings, in which.

DESCRIPTION OF SPECIFIC EMBODIMENTS

Figure 1A:
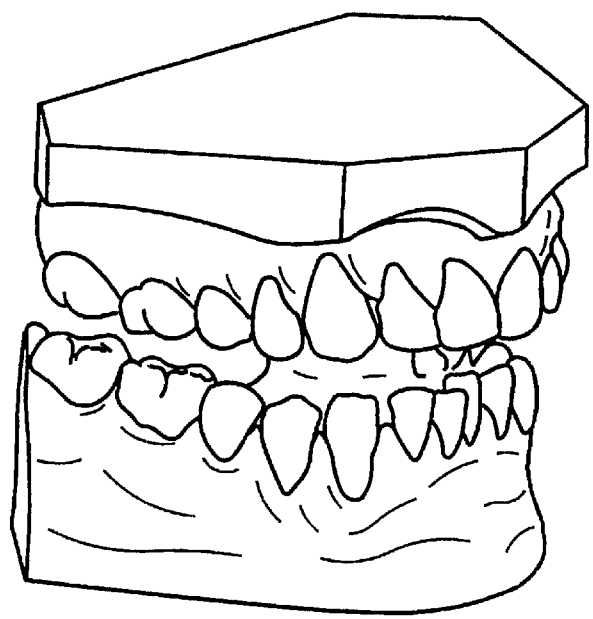
FIGS. 1A–B are two schematic illustrations of respective views of a virtual 3D dental model.
Figure 1B:
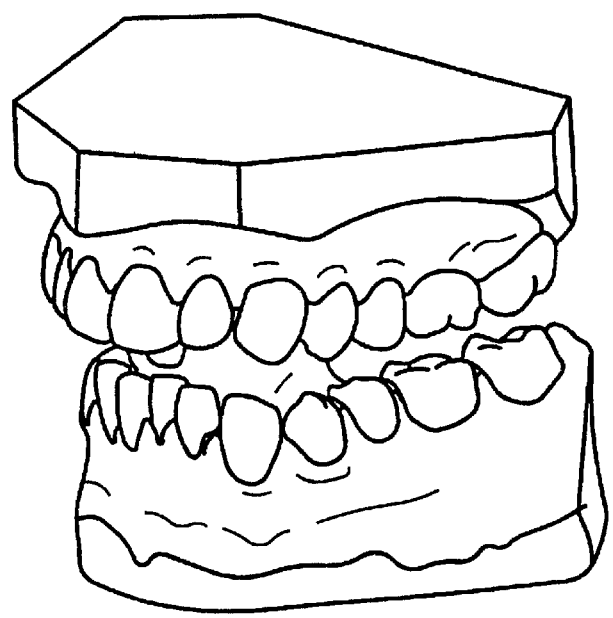
Figure 2:
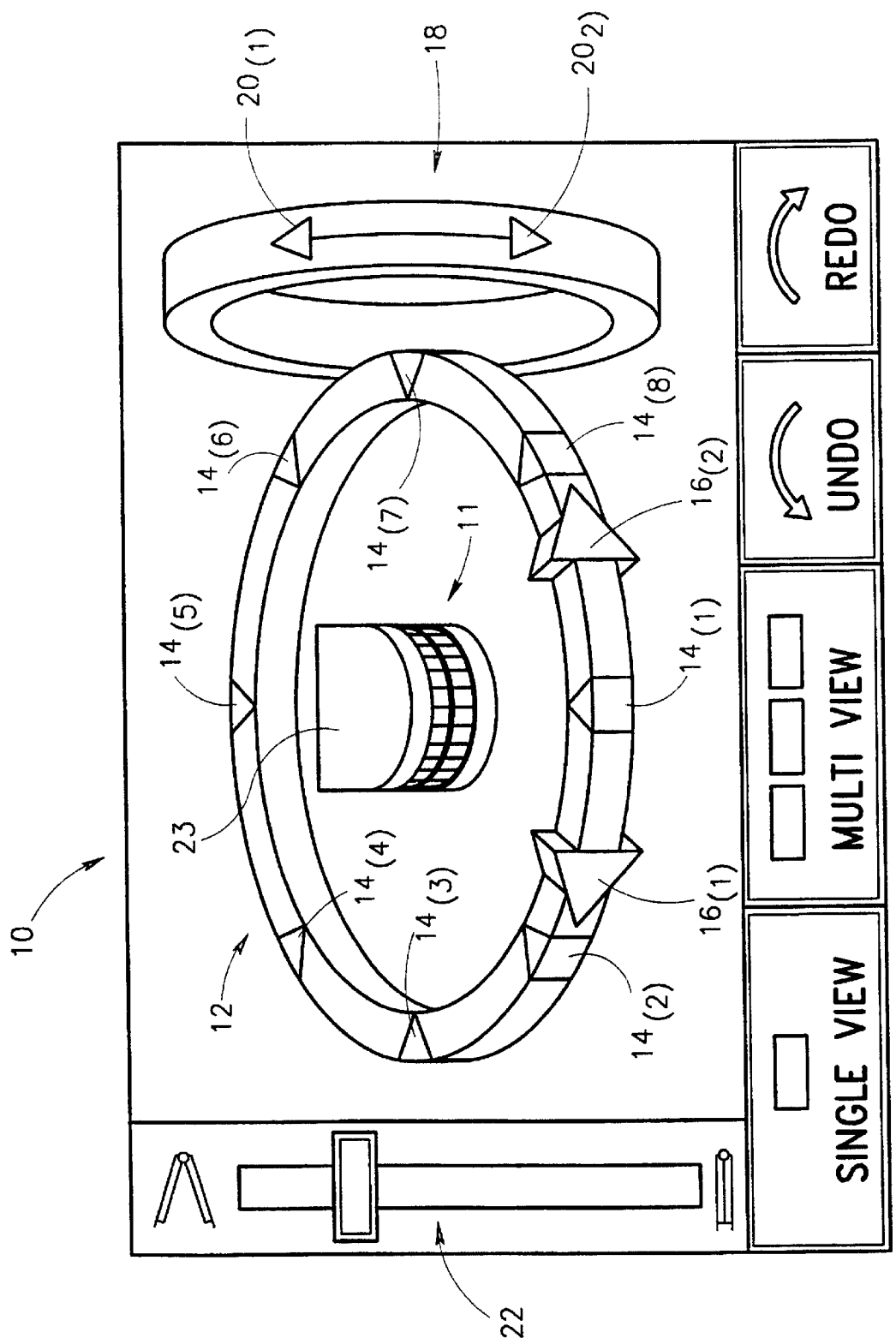
FIG. 2 is a schematic illustration of a GUI, according to one embodiment of the invention.

Attention is directed to FIG. 2, illustrating a view control box (referred to also as GUI), according to one embodiment of the invention. By a non limiting example, the specified view control box is realized as an icon 10 of the kind provided by Windows 95 operating system, commercially available from Microsoft, Inc. Whilst not shown in FIG. 2, the specified GUI is portrayed on a conventional display device that is coupled to, e.g. a conventional P.C. accommodating also a Central Processing Unit (CPU), storage means and an input device, such as mouse.

The GUI of FIG. 2 provides a minimized virtual 3D dental model 11, encircled by a graphic symbol (ring) 12 bearing eight graphic symbols $14_{(1)}$ to $14_{(8)}$ indicative of eight respective preset views of the dental model, with each two consecutive views shifted by 45° one with respect to the other.

Figure 3:
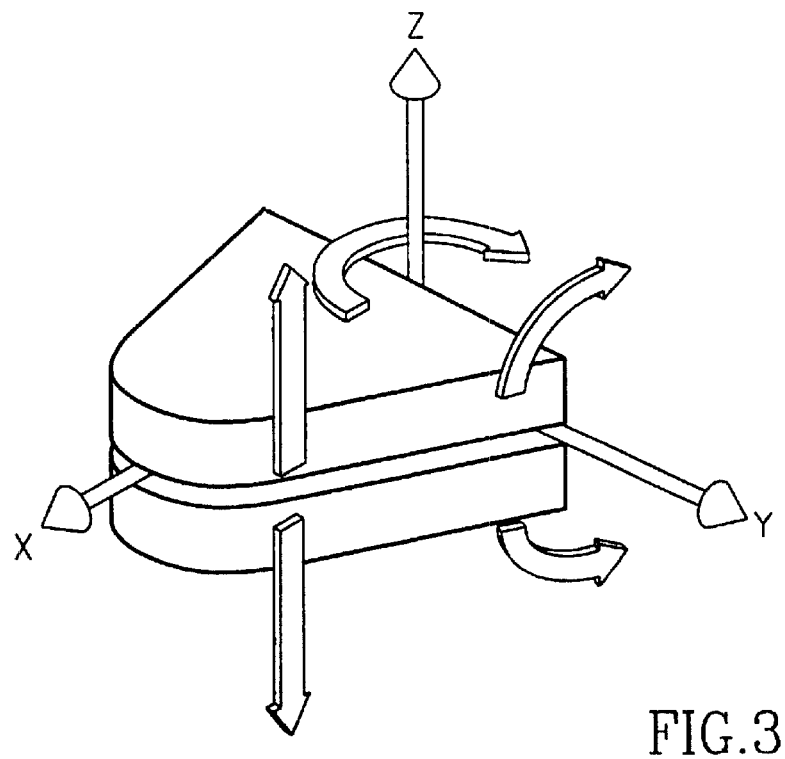
FIG. 3 is a schematic illustration of a model in an XYZ coordinate system.

The preset view $14_{(1)}$ corresponds to the front view of the model (i.e. along the X axis as depicted in FIG. 3) and the remaining seven preset views are shifted by 45° increments each.

If, for example, a conventional mouse is used as an input device, any click on one of the specified graphic symbols $14_{(1)}$ to $14_{(8)}$, will result in displaying the model from the preset view that correspond to the selected graphic symbol.

Consider, for example, that the default display of the dental model is the preset view that corresponds to graphic symbol $14_{(1)}$ (i.e front view), and that the user selects graphic symbol $14_{(3)}$. The virtual dental model will then be viewed with 90° shift (as will be explained in greater detail with reference to FIG. 4, below), and this may be realized according to known per se rotating techniques such as "J. D. Foley and A. Van Dam, "Fundamentals of Interactive Computer Graphics".

Selecting graphic symbols $16_{(1)}$ and $16_{(2)}$ results in respective clockwise (CW) and counter clockwise (CCW) continuous rotation of the model between the preset views, or in other words it provides for an indefinite number of preset views of the dental model.

Clicking on graphic symbol 18 will result in elevating the model, as will be explained in greater detail below.

By this particular embodiment, clicking on the graphic symbol $20_{(1)}$ will result in elevating the model in the direction prescribed by arrow $20_{(1)}$, whereas clicking on the graphic symbol $20_{(2)}$ will result in elevating the model in the direction prescribed by arrow $20_{(2)}$.

By this particular embodiment, the closer the mouse cursor to the arrow head, the faster the elevation.

The elevation operation may be realized according to known per se techniques e.g. J. D. Foley and A. Van Dam ibid.

The graphic symbols illustrated in FIG. 2 are, of course, only examples. Whenever required, graphic symbols may include also text, and/or may bring about sound effect.

Preferably, icon 10 is displayed in minimized form whereas the model itself, after having been brought to the preset view, is displayed in a separate window having scalable window size. Preferably, the window size is manipulated by utilizing built-in operating system primitives.

If desired, indication as to the point in space from which the specified preset view is observed, may be also provided by the GUI of FIG. 2.

Figure 4:
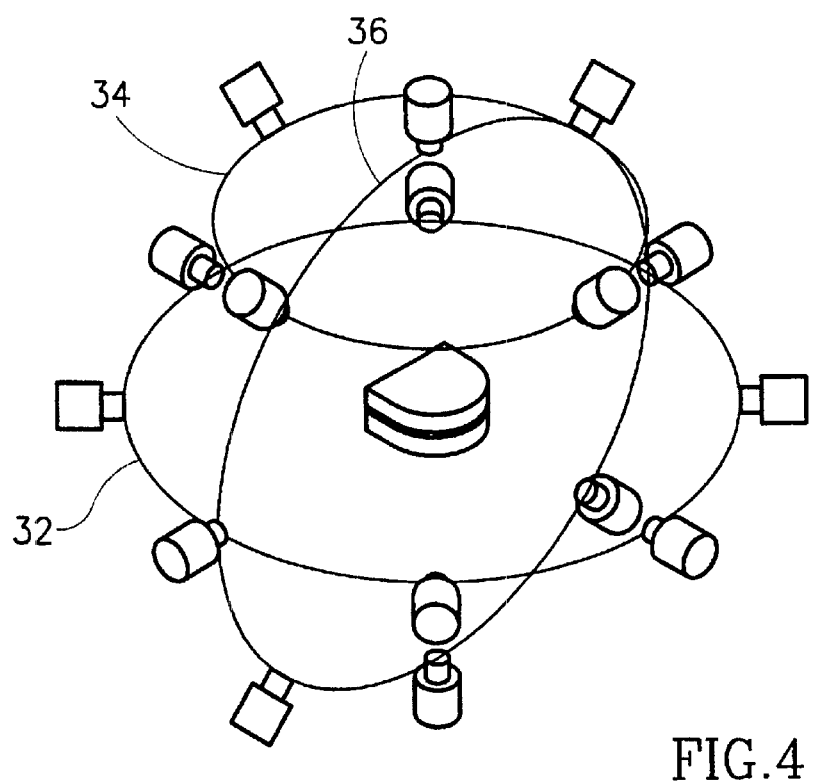
FIG. 4 is an illustrative representation of several preset views of a model, as captured by means of virtual cameras positioned on latitude and meridian lines of a sphere.

The rotation and elevation operations referred to in FIG. 2, may be represented, for illustrative purposes, as pre-set views that are captured by respective virtual cameras positioned or moving along a coordinate system superimposed on a virtual surface, e.g. a sphere, surrounding and being essentially concentric with the dental model (FIG. 4).

Representative, yet not exclusive, example of such a coordinate system is latitude and meridian lines.

Those versed in the art will readily appreciate that a sphere is only one possible closed two dimensional surface of 3D space that surrounds the dental model and accordingly by yet another non-limiting example, the virtual cameras move on a surface of ellipsoid that surrounds the dental model.

Thus, circles 32 and 34 illustrate two, out of virtually an indefinite number, of possible horizontal circles along which the cameras can move.

As shown, eight preset virtual cameras are placed along circle 32, with each camera capturing a given preset view as selected by graphic symbols $14_{(1)}$ to $14_{(8)}$, respectively (see FIG. 2). Likewise, four cameras which correspond to four preset views are placed along circle 34, each camera angularly shifted by 90° with respect to adjacent camera. The specified four views are selected by graphic symbols $14_{(1)}$, $14_{(3)}$, $14_{(5)}$ and $14_{(7)}$, respectively. Since circle 32 in effectively co-planner with the occlusion plane of the model, the optical axis of the virtual cameras reside in the XY plane of the XYZ coordinate system preferably so as to maintain the dental model in optimal zoom. Conversely, since circle 34 is elevated with respect to circle 32, the optical axis of the virtual cameras are tilted downwardly towards the model with respect to the XY plane of the XYZ coordinate system preferably in order to maintain the latter in optimal zoom.

When moving along circle 34, the elevation is retained, i.e. moving along a plane which is essentially parallel to the occlusion plane.

Occlusion plane is this context is defined as "Horizontal plane through the tips of the buccal cusps of the premolars or the tips of the mesiobuccal cusps of the first molars and first premolars" (see Color atlas of dental medicine, orthodont diagnosis, by Thomas Rakoski)

In order to move from one horizontal circle to the other the cameras can move along vertical circle 36, which as specified before is realized by known per se rotating techniques.

Preferably, the GUI also provides for graphic symbols representative of "OPEN JAW", "CLOSE JAW", (22 in FIG. 2). The latter may be realized, e.g. by following the technique disclosed in "Joseph A. Gibilisko DDS, Charles McNeill DDS and Harold T. Perry DDS, "Orofacial Pain".

By this particular embodiment, the dental model 11 itself also constitutes a graphic symbol, i.e. clicking on the upper jaw 23 will render it transparent, further click will render it blank, and yet further click will revert it to normal, as depicted in FIG. 2.

The proposed GUI of the invention may, of course, be incorporated into the GUI as provided for example by the operating system. Thus, by way of example, insofar as the GUI of a Windows-based operating system is concerned (version 3.x or 95), the desired preset view of the model may be portrayed on one window whilst other predetermined views may be portrayed simultaneously on different windows, thereby providing multiple views of the dental model (multi-view display mode).

Figure 5:
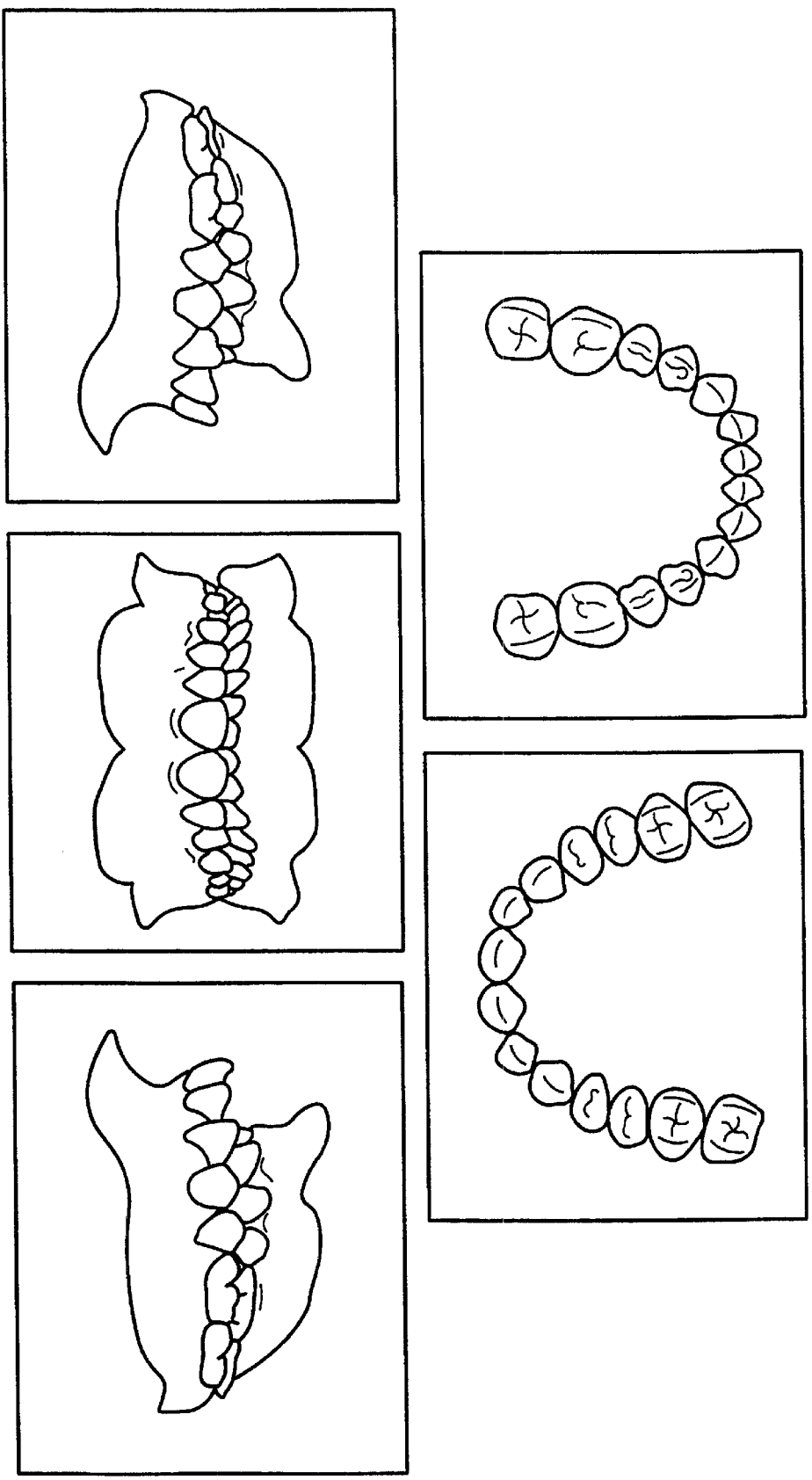
FIG. 5 is a schematic illustration of five different views of a model portion in a multi-view display mode of operation.

A typical, yet not exclusive, example of the additional windows in a multi-view display mode is depicted in FIG. 5, showing respective left, front, right, maxilla and mandibular, views of the individual's dental arches.

The present invention has been described with a certain degree of particularity, but it should be understood that various alterations and modifications can be made withoudeparting from the spirit or scope of the invention as hereinafter claimed. t

What is claimed is:

1. A method for displaying a virtual three dimensional (3D) dental model at desired pre-set views, for orthodontic use on a display device of a computer system comprising a Central Processing Unit, an associated input device, storage device and said display device, the virtual 3D dental model being stored on said storage device and being indicative of at least a 3D structure of an individual's dental arches, the method comprising the steps of:

(a) providing a graphic user interface (GUI) that includes a graphic representation of the dental model and a plurality of graphic symbols, each representative of at least one desired pre-set view of the dental model or a portion thereof from respective desired directions, said plurality of graphic symbols corresponding to respective front view of the model and other pre-set views which are shifted one with respect to the other, wherein at least several of said pre-set views correspond to views captured by virtual cameras positioned or moving along a coordinate system superimposed on a virtual closed two dimensional surface of 3D space that surrounds said dental model and is essentially concentric therewith;

(b) selecting through said input device a graphic symbol from among said plurality of graphic symbols;

(c) responsive to the selection of said graphic symbol, moving the dental model or portion thereof to at least one preset view which corresponds to said graphic symbol, whilst retaining the model essentially in zoom.

2. The method according to claim 1, wherein said two dimensional surface is a spherical surface.

3. The method according to claim 1, wherein said two dimensional surface is an ellipsoidal surface.

4. The method according to claim 1, further comprising at least one graphic symbol for facilitating continuous movement of the model, thereby attaining a succession of an indefinite number of pre-set views of said model.

5. The method according to claim 1, wherein said GUI is portrayed as an icon on said display device and the dental model stipulated in step (c) is portrayed on a separate window, on said display device.

6. The method according to claim 5, wherein further simultaneous respective pre-set views of said model or portion thereof, are portrayed on other windows.

7. The method according to claim 1, further comprising graphical symbols representative of either or both of open and close jaw preset views.

8. The method according to claim 1, further comprising indication as to the point in space from which the specified preset view is observed.

9. The method of claim 1, wherein at least several of said pre-set views correspond to views captured by virtual cameras positioned or moving along substantially at least two latitude lines and substantially meridian lines of a virtual closed two dimensional surface of 3D space that surrounds said dental model and is essentially concentric therewith.

10. The method of claim 9, wherein said GUI comprises a minimized virtual 3D dental model encircled by a graphic symbol that constitutes a ring bearing plurality of graphic symbols indicative of respective pre-set views of the dental model, with each two consecutive views shifted one with respect to the other, along selected substantially latitude line;

said ring further bearing graphic symbols for respective clockwise and counter clockwise continuous rotation of the model between selected pre-set views along said substantially latitude line;

the GUI further including a vertical ring constituting a graphic symbol for altering the elevation of the model along selected substantially meridian line;

said vertical ring bearing graphic symbols for elevating the model in respective upward and downward elevation along said substantially meridian line.

11. The method according to claim 1, wherein said front view and said plurality of graphic symbols are shifted by 45° with respect to each other.

12. The method according to claim 1, wherein said front view and said plurality of graphic symbols are shifted by 90° with respect to each other.

13. A computer system comprising a Central Processing Unit and an associated input device, storage device and display device, the computer system being adapted to display on said display device virtual three dimensional (3D) dental model at desired pre-set views, for orthodontic use, the virtual 3D dental model being stored on said storage device and being indicative of at least a 3D structure of an individual's dental arches; the computer system comprising:

(a) a graphic user interface (GUI) that includes a graphic representation of the dental model and a plurality of graphic symbols each representative of at least one desired pre-set view of the dental model or a portion thereof from respective desired directions, said plurality of graphic symbols corresponding to respective front view of the model and other pre-set views which are shifted one with respect to the other, wherein at least several of said pre-set views correspond to views captured by virtual cameras positioned or moving along a coordinate system superimposed on a virtual closed two dimensional surface of 3D space that surrounds said dental model and is essentially concentric therewith;

(b) means responsive to activation of said input device for selecting a graphic symbol from among said plurality of graphic symbols;

(c) means responsive to the selection of said graphic symbol, for moving the dental model or portion thereof to at least one pre-set view which corresponds to said graphic symbol, whilst retaining the model essentially in zoom.

14. A computer system as in claim 13, wherein said two dimensional surface is a spherical or an ellipsoidal surface.

15. A computer system as in claim 13, further comprising at least one graphic symbol for facilitating continuous movement of the model, thereby attaining a succession of an indefinite number of pre-set views of said model.

16. A computer system as in claim 13, wherein said GUI is portrayed as an icon on said display device and said dental model is portrayed on a separate window, on said display device.

17. A computer system as in claim 13, wherein further simultaneous respective pre-set views of said model or position thereof are portrayed on other windows.

18. A computer system as in claim 13, further comprising graphical symbols representative of either or both of open and close jaw pre-set views.

19. A computer system as in claim 13, further comprising indication as to the point in space from which the specified pre-set view is observed.

20. A computer system as in claim 13, wherein at least several of said pre-set views correspond to views captured by virtual cameras positioned or moving along substantially at least two latitude lines and substantially meridian lines of a virtual closed two dimensional surface of 3D space that surrounds said dental model and is essentially concentric therewith.

21. A computer system as in claim 20, wherein said GUI comprises:

a minimized virtual 3D dental model encircled by a graphic symbol that constitutes a ring bearing plurality of graphic symbols indicative of respective pre-set views of the dental model, with each two consecutive views shifted one with respect to the other, along selected substantially latitude line;

said ring further bearing graphic symbols for respective clockwise and counter clockwise continuous rotation of the model between selected pre-set views along said substantially latitude line;

the GUI further including a vertical ring constituting a graphic symbol for altering the elevation of the model along selected substantially meridian line;

said vertical ring bearing graphic symbols for elevating the model in respective upward and downward elevation along said substantially meridian line.

22. A computer system according to claim 13, wherein said front view and said plurality of graphic symbols are shifted by 45° with respect to each other.

23. A computer system according to claim 13, wherein said front view and said plurality of graphic symbols are shifted by 90° with respect to each other.

24. A computer readable medium comprising instructions for causing a computer system comprising a Central Processing Unit and an associated input device, storage device and display device, to perform a method for displaying on said display device a virtual three dimensional (3D) dental model at desired pre-set views, for orthodontic use, the virtual 3D dental model being stored on said storage device and being indicative of at least a 3D structure of an individual's dental arches, the method comprising the steps of:

(a) providing a graphic user interface (GUI) that includes a graphic representation of the dental model and a plurality of graphic symbols, each representative of at least one desired pre-set view of the dental model or a portion thereof from respective desired directions, said plurality of graphic symbols corresponding to respective front view of the model and other pre-set views which are shifted one with respect to the other, wherein at least several of said pre-set views correspond to views captured by virtual cameras positioned or moving along a coordinate system superimposed on a virtual closed two dimensional surface of 3D space that surrounds said dental model and is essentially concentric therewith, (b) responsive to the selection of a graphic symbol from among said plurality of graphic symbols through said input device, moving the dental model or portion thereof to at least one pre-set view which corresponds to said graphic symbol, whilst retaining the model essentially in zoom.

25. A computer readable medium as in claim 24, said two dimensional surfaces being a spherical or an ellipsoidal surface.

26. A computer readable medium as in claim 24, further storing data for portraying said GUI as an icon on a display device and the dental model on a separate window, on said display device.

27. A computer readable medium as in claim 26, further storing data for simultaneously portraying, on other windows, further respective pre-set views of said model or portion thereof.

28. A computer readable medium as in claim 24, further storing data for displaying graphical symbols representative of either or both of open and closed jaw pre-set views.

29. A computer readable medium as in claim 24, further storing data for indicating as to the point in space from which the specified pre-set view is observed.

30. A computer readable medium as in claim 24, wherein at least several of said pre-set views correspond to views captured by virtual cameras positioned or moving along substantially at least two latitude lines and substantially meridian lines of a virtual closed two dimensional surface of 3D space that surrounds said dental model and is essentially concentric therewith.

31. A computer readable medium as in claim 30, further storing data for displaying:

a minimized virtual 3D dental model encircled by a graphic symbol that constitutes a ring bearing plurality of graphic symbols indicative of respective pre-set views of the dental model, with each two consecutive views shifted one with respect to the other, along selected substantially latitude line;

said ring further bearing graphic symbols for respective clockwise and counter clockwise continuous rotation of the model between selected pre-set views along said substantially latitude line;

the GUI further including a vertical ring constituting a graphic symbol for altering the elevation of the model along selected substantially meridian line;

said vertical ring bearing graphic symbols for elevating the model in respective upward and downward elevation along said substantially meridian line.

32. A computer readable medium according to claim 24, wherein said front view and said plurality of graphic symbols are shifted by 45° with respect to each other.

33. A computer readable medium according to claim 24, wherein said front view and said plurality of graphic symbols are shifted by 90° with respect to each other.

\* \* \* \* \*